United States Patent [19]

Regnier et al.

[11] 4,010,267
[45] Mar. 1, 1977

[54] BENZODIOXOLE COMPOUNDS

[75] Inventors: Gilbert Regnier, Hatenay-Malabry; Roger Canevari, Villebon-sur-Yvette; Michel Laubie, Vaucresson; Jean-Claude Poignant, Bures-sur-Yvette, all of France

[73] Assignee: Science Union et Cie, Societe Francaise de Recherche Medical, Suresnes, France

[22] Filed: Mar. 26, 1975

[21] Appl. No.: 562,226

Related U.S. Application Data

[62] Division of Ser. No. 342,284, March 16, 1973, Pat. No. 3,917,597.

[30] Foreign Application Priority Data

Apr. 7, 1972 United Kingdom ............ 16098/72

[52] U.S. Cl. .................... 424/250; 260/268 TR; 260/268 BC
[51] Int. Cl.² ........................................ C07D 295/08
[58] Field of Search ............. 260/268 BC, 268 TR; 424/250

[56] References Cited

UNITED STATES PATENTS 3,299,067  1/1967  Regnier et al. ............ 260/256.4 N
3,585,193  6/1971  Regnier et al. ............ 260/268 BC Primary Examiner—Paul M. Coughlan, Jr.
Attorney, Agent, or Firm—Gordon W. Hueschen

[57]  ABSTRACT

Benzodioxole compounds of the formula: vasodilator

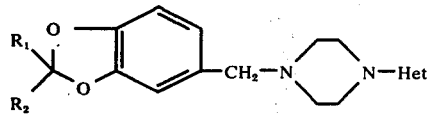

wherein $R_1$ is hydrogen, lower alkyl, aryl, haloaryl, lower-alkylaryl, lower-alkoxyaryl, methylenedioxyaryl, ethylenedioxyaryl, trifluoromethylaryl, nitroaryl or aminoaryl, $R_2$ is lower-alkyl, aryl, haloaryl, lower-alkylaryl, lower-alkoxyaryl, methylenedioxyaryl, ethylenedioxyaryl, trifluoromethylaryl, nitroaryl or aminoaryl, or $R_1 + R_2$ are $-(CH_2)_4-$, $-(CH_2)_5-$ or $-(CH_2)_6-$ and Het is pyridyl, pyrimidinyl, pyridazinyl, pyrazinyl, quinazolinyl, 1,3,5 triazinyl or 1,3-thiazolyl, each being optionally substituted by lower-alkyl, lower-alkoxy, hydroxyl or phenyl.

These compounds are used as medicines especially as peripheral vasocilator agent and central nervous system stimulant.

13 Claims, No Drawings

BENZODIOXOLE COMPOUNDS

This is a Division of application Ser. No. 342,284, filed Mar. 16, 1973, U.S. Pat. No. 3,917,597.

The present invention provides benzodioxole compounds of the general formula I:

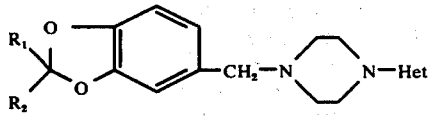

wherein:

$R_1$ is selected from the group consisting of a hydrogen atom, an alkyl radical having from 1 to 5 carbon atoms inclusive, an unsubstituted aryl radical and an aryl radical substituted by on or more substituents selected from the group consisting of halogen atoms, for example fluorine and chlorine atoms, alkyl and alkoxy radicals each having from 1 to 5 carbon atoms inclusive, methylenedioxy, ethylenedioxy, trifluoromethyl, nitro and amino radicals;

$R_2$ is selected from the group consisting of an alkyl radical having from 1 to 5 carbon atoms inclusive, an unsubstituted aryl radical and an aryl radical substituted by one or more substituents selected from the group consisting of halogen atoms, for example fluorine and chlorine atoms, alkyl and alkoxy radicals each having from 1 to 5 carbon atoms inclusive, methylenedioxy, ethylenedioxy, trifluoromethyl, nitro and amino radicals; and $R_1$ and $R_2$ together represent a polymethylenic chain of the formula $-(CH_2)_n-$ wherein n is selected from 4, 5 and 6 ; and Het is a heterocyclic radical containing from 1 to 3 nitrogen atoms and optionally one sulfur atom, selected from the group consisting of pyridyl, pyrimidinyl, pyridazinyl, pyrazinyl, quinazolinyl, 1,3,5-triazinyl and 1,3-thiazolyl radicals and each of these radicals substituted by one or more substituents selected from the group consisting of alkyl and alkoxy radicals each having from 1 to 5 carbon atoms inclusive, hydroxyl and phenyl radicals ; and, acid addition salts, especially physiologically tolerable acid addition salts, thereof.

The compounds of the general formula I are new. They were prepared by condensing a compound of the general formula II :

Het — Z 

wherein Het has the meanings given above and Z represents a chlorine or bromine atom, with a compound of the general formula III :

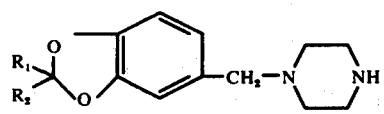

wherein $R_1$ and $R_2$ have the meaning given above, and also, by condensing a compound of the general formula IV :

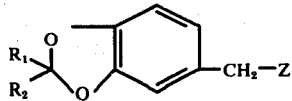

with a compound of the general formula V :

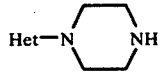

wherein Z, $R_1$, $R_2$ and Het have the meanings given above.

The condensation processes of the invention are advantageously carried out in a polar solvent, for example in an alcohol having a high boiling point, for example butanol or pentanol or, preferably, in an aliphatic amide for example dimethylformamide or dimethylacetamide, or in an nonpolar solvent such as an aromatic hydrocarbon, for example toluene or xylene. The processes are advantageous carried out at a temperature within the range of from 110° to 140° C in the presence of an acceptor of the hydrogen halide formed during the reaction. As an acceptor there may be used, for example, an alkali or alkaline earth metal salt of carbonic acid, for example sodium or potassium bicarbonate or carbonate or calcium carbonate, a tertiary organic base, for example dimethylaniline, pyridine or triethylamine or an excess of the compound of the formula III or V.

The compounds of the present invention are weak bases which may be converted with acids into acid addition salts. As acids used to form these salts, there may be especially mentioned, for example, in the mineral series : hydrochloric, hydrobromic, sulfuric and phosphoric acids and in the organic series : acetic, propionic, maleic, fumaric, tartaric, citric, oxalic, benzoic, methanesulfonic and isethionic acids.

The compounds of the general formula I and acid addition salts thereof may be purified by, for example, crystallisation or chromatographic absorption.

The following examples illustrate the invention. The melting points were determined in a capillary tube (cap.) or on a Kofler block (K).

EXAMPLE 1

5-[4-(2-pyrimidinyl)-1 -piperazinyl] methyl-2-phenyl benzo [d]-1,3-dioxole

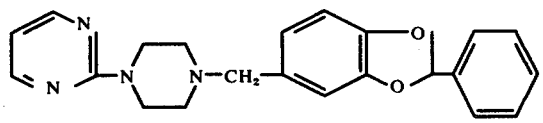

A solution of 8.5 g (0.0344 mole) of 5-chloromethyl-2-phenyl benzo [d]-1,3-dioxole (BP/0.05 mm = 135°–137° C) and 11.3 g (0.0689 mole) of 1-(2-pyrimidinyl) piperazine in 250 ml of anhydrous xylene was refluxed for 9 hours. The precipitate of 1-(2-pyrimidinyl) piperazine hydrochloride formed was suction-filtered off and the xylene was evaporated off under reduced pressure.

The residual crystallised product was washed with water and was then recrystallised from 70 ml of cyclohexane. There was obtained 10.2 g of 5-[4-(2-pyrimidinyl)-1-piperazinyl] methyl-2-phenyl benzo [d]-1,3-dioxole, cream-coloured crystals melting at (K) 106° C.

The starting compound, 5-chloromethyl-2-phenyl benzo [d]-1,3-dioxole ($n_D^{25} = 1.597$) was prepared by chlorination, with $SOCl_2$, of 5-hydroxymethyl-2-phenyl benzo [d]-1,3-dioxole melting (K) at 75° C, itself prepared by reduction, with Li Al $H_4$, of 5-carbomethoxy-2-phenyl benzo [d]-1,3-dioxole, B.P./0.05 mm = 155° to 157° C, $n_D^{25} = 1.583$.

EXAMPLES 2–24

The following compounds were prepared by processes analogous to the process described in Example 1.

2. 5-[4-(2-pyrimidinyl)-1-piperazinyl] methyl-2-methyl-2-ethyl benzo [d]-1,3-dioxole, M.P. (cap.) 90°–92° C (petroleum ether), starting from 1-(2-pyrimidinyl) piperazine and 5-bromomethyl-2-methyl-2-ethyl benzo [d]-1,3-dioxole. This bromo derivative was prepared by bromination of 2,5-dimethyl-2-ethyl benzo [d]-1,3-dioxole, (B.P./20 mm : 102° C, $n_D^{25}$ : 1.5002) with N-bromo-succinimide in carbon tetrachloride and benzoyl peroxide.

3. 5-[4-(2-pyrimidinyl)-1-piperazinyl] methyl-2,2-cyclopentamethylene benzo [d]-1,3-dioxole, M.P. (cap) 85-88° C. (petroleum ether), starting from 1-(2-pyrimidinyl) piperazine and 5-bromomethyl-2,2-cyclopentamethylene benzo [d]-1,3-dioxole. This bromo derivative was prepared by bromination of 5-methyl-2,2-cyclopentamethylene benzo [d]-1,3-dioxole (B.P./0.05 mm = 94° C, $n_D^{25} = 1.5297$) with N-bromosuccinimide in carbon tetrachloride and benzoyl peroxide.

4. 5-[4-(2-pyrimidinyl)-1-piperazinyl] methyl-2,2-cyclotetramethylene benzo [d]-1,3-dioxole, M.P. (cap.) 72°–74° C (cyclohexane), starting from 1-(2-pyrimidinyl) piperazine and 5-bromomethyl-2,2-cyclotetramethylene benzo [d]-1,3-dioxole.

5. 5-[4-(2-pyrimidinyl)-1 piperazinyl] methyl-2,2-cyclohexamethylene benzo [d]-1,3-dioxole, M.P. (cap.) 80°–83° C (petroleum ether), starting from 1-(2-pyrimidinyl) piperazine and 5-bromomethyl-2,2-cyclohexamethylene benzo [d]-1,3-dioxole.

6. 5-[4-(2-pyrimidinyl)-1 piperazinyl] methyl-2-methyl benzo [d]-1,3-dioxole, M.P. (cap.) of the corresponding monohydrochloride : 270°–272° C (methanol), starting from 1-(2-pyrimidinyl) piperazine and 5-bromomethyl-2-methyl benzo [d]-1,3-dioxole.

7. 5-[4-(2-pyrimidinyl)-1-piperazinyl] methyl-2-p. fluorophenyl benzo [d]-1,3-dioxole, M.P. (K.) 102° C (methanol), starting from 1-(2-pyrimidinyl) piperazine and 5-chloromethyl-2-p. fluorophenyl benzo [d]-1,3-dioxole.

8. 5-[4-(2-pyrimidinyl)-1-piperazinyl] methyl-2-m. fluorophenyl benzo [d]-1,3-dioxole, M.P. (cap.) of the corresponding dihydrochloride 220°–223° C (anhydrous ethanol), starting from 1-(2-pyrimidinyl) piperazine and 5-chloromethyl-2-m. fluorophenyl benzo [d]-1,3-dioxole.

9. 5-[4-(2-pyrimidinyl)-1-piperazinyl] methyl-2-m. tolyl benzo [d]-1,3-dioxole, M.P. (cap.) of the corresponding dihydrochloride : 212°–214° C (anhydrous methanol), starting from 1-(2-pyrimidinyl) piperazine and 5-chloromethyl-2-m. tolyl benzo [d]-1,3-dioxole.

10. 5-[4-(2-pyrimidinyl)-1-piperazinyl] methyl-2-m. methoxyphenyl benzo [d]-1,3-dioxole, M.P. (cap.) of the corresponding dihydrochloride : 208°–212° C (ethanol), starting from 1-(2-pyrimidinyl) piperazine and 5-chloromethyl-2-m. methoxyphenyl benzo [d]-1,3-dioxole.

11. 5-[4-(2-pyrimidinyl)-1-piperazinyl] methyl-2-m. trifluoromethylphenyl benzo [d]-1,3-dioxole, M.P. (cap.) of the corresponding dihydrochloride : 221°–230° C with decomposition (methanol), starting from 1-(2-pyrimidinyl) piperazine and 5-chloromethyl-2-m. trifluoromethylphenyl benzo [d]-1,3-dioxole.

12. 5-[4-(4-pyrimidinyl)-1-piperazinyl] methyl-2-methyl benzo [d]-1,3-dioxole, M.P. (cap.) of the corresponding dihydrochloride : 225°–228° C (ethanol), starting from 1-(4-pyrimidinyl) piperazine and 5-bromomethyl-2-methyl benzo [d]-1,3-dioxole.

13. 5-[4-(2-pyridyl)-1-piperazinyl] methyl-2-methyl benzo [d]-1,3-dioxole, M.P. (cap.) of the corresponding dihydrochloride : 213°–215° C (anhydrous methanol), starting from 1-(2-pyridyl) piperazine and 5-bromomethyl-2-methyl benzo [d]-1,3-dioxole.

14. 5-[4-(6-methoxy-2-pyridyl)-1-piperazinyl] methyl-2-methyl benzo [d]-1,3-dioxole, M.P. (cap.) of the corresponding monohydrochloride : 223°–225° C (anhydrous methanol), starting from 1-(6-methoxy-2-pyridyl) piperazine and 5-bromomethyl-2-methyl benzo [d]-1,3-dioxole.

15. 5-[4-(3-pyridazinyl)-1-piperazinyl] methyl-2-methyl benzo [d]-1,3-dioxole, M.P. (cap.) 92°–94° C (cyclohexane), starting from 1-(3-pyridazinyl) piperazine and 5-bromomethyl-2-methyl benzo [d]-1,3-dioxole.

16. 5-[4-(2-pyrazinyl)-1-piperazinyl] methyl-2,2-cyclopentamethylene benzo [d]-1,3-dioxole, M.P. (cap.) 80°–83° C (petroleum ether), starting from 1-(2-pyrazinyl) piperazine and 5-bromomethyl-2,2-cyclopentamethylene benzo [d]1,3-dioxole.

17. 5-[4-(6-methyl-2-pyrazinyl)-1-piperazinyl] methyl-2-methyl benzo [d]-1,3-dioxole, M.P. (cap.) of the corresponding dihydrochloride : 208°–209° C (anhydrous ethanol), starting from 1-(6-methyl-2-pyrazinyl) piperazine and 5-bromomethyl-2-methyl benzo [d]-1,3-dioxole.

18. 5-[4-(2-quinazolinyl)-1 piperazinyl] methyl-2-methyl benzo[d]-1,3-dioxole, M.P. (cap.) 111°–112° C (ethanol), starting from 1-(2-quinazolinyl) piperazine and 5-bromomethyl-2-methyl benzo [d]-1,3-dioxole.

19. 5-[4-(2-thiazolyl)-1-piperazinyl] methyl-2-methyl benzo [d]-1,3-dioxole, M.P. (cap.) 78°–79° C (methanol), starting from 1-(2-thiazolyl) piperazine and 5-bromomethyl-2-methyl benzo [d]-1,3-dioxole.

20. 5-[4-(4-methyl-2-thiazolyl)-1-piperazinyl] methyl-2-methyl benzo [d]-1,3-dioxole, starting from 1-(4-methyl-2-thiazolyl) piperazine and 5-bromomethyl-2-methyl benzo [d]-1,3-dioxole.

21. 5-[4-(4-phenyl-2-thiazolyl)-1-piperazinyl] methyl-2-methyl benzo [d]-1,3-dioxole, starting from 1-(4-phenyl-2-thiazolyl) piperazine and 5-bromomethyl-2-methyl benzo [d]-1,3-dioxole.

22. 5-[4-(4,5-dimethyl-2-thiazolyl)-1-piperazinyl] methyl-2-methyl benzo [d]-1,3-dioxole, starting from 1-(4,5-dimethyl-2-thiazolyl) piperazine and 5-bromomethyl-2-methyl benzo [d]-1,3-dioxole.

23. 5-[4-(5-methyl-2-thiazolyl)-1-piperazinyl] methyl-2-methyl benzo [d]-1,3-dioxole, starting from 1-(5-methyl-2-thiazolyl) piperazine and 5-bromomethyl-2-methyl benzo [d]-1,3-dioxole.

24. 5-[4-(5-phenyl-2-thiazolyl)-1-piperazinyl] methyl-2 methyl benzo [d]-1,3-dioxole, starting from 1-(5-phenyl-2-thiazolyl) piperazine and 5-bromomethyl-2-methyl benzo [d]-1,3-dioxole.

EXAMPLE 25

5-[4-(2-pyrimidinyl)-1-piperazinyl] methyl-2-phenyl benzo [d]-1,3-dioxole

A solution of 5.7 g (0.05 mole) of 2-chloropyrimidine and 14.7 g (0.05 mole) of 5-(1-piperazinyl methyl)-2-phenyl benzo [d]-1,3-dioxole in 200 ml of dimethylformamide was refluxed for 9 hours in the presence of 13.8 g of dry potassium carbonate. The so-obtained salt was suction-filtered off and the solvent was evaporated off under reduced pressure. The crystallised residue was washed with water, and was then recrystallised from 110 ml of cyclohexane. There was obtained 15.2 g of 5-[4-(2-pyrimidinyl)-1 piperazinyl] methyl-2-phenyl benzo [d]-1,3-dioxole, cream-coloured crystals melting at (K) 106° C.

The starting compound, 5-(1-piperazinyl methyl)-2-phenyl benzo [d]-1,3-dioxole, was prepared by heating, at 140° C, 5-chloromethyl-2-phenyl benzo [d]-1,3-dioxole with an excess of anhydrous piperazine.

The compounds of Examples 2 to 24 were also prepared according to the process described in Example 25.

The compounds of the present invention and physiologically tolerable salts thereof possess valuable pharmacological and therapeutic properties, especially peripheral vasodilator and central nervous system stimulant properties.

Their toxicity expressed in $LD_{50}$ in mice varies from 125 to > 1000 mg/kg by intraperitoneal route.

When administered to the dog intravenously at doses of 0.5 to 5.0 mg/kg, an increase of the femoral output of 20 to 100 % is observed durably.

The scores of CNS stimulation or stereotypy were determined by the method of Quinton and Haliwell, Nature 200, 178 (1963). Scores of up to 208 were observed with doses of 20 to 80 mg/kg I.P.

These results permit the use of the present compounds in therapy, especially in the treatment of vasoconstriction or obliteration, as well as in CNS depression, particularly in parkinsonism.

The present invention also provides pharmaceutical compositions containing a compound of general formula I or a physiologically tolerable salt thereof in admixture of conjunction with a pharmaceutically suitable carrier, such, for example, as distilled water, glucose, lactose, starch, talc, magnesium stearate, ethyl cellulose or cocoa butter.

The so-obtained pharmaceutical compositions may be in form of tablets, dragees, capsules, suppositories or injectable or drinkable solutions and may be administered by oral, rectal or parenteral route at doses of 20 to 200 mg, 1 to 5 times a day.

We claim:

1. A compound selected from the group consisting of:
   A. benzodioxole compounds of the general formula:

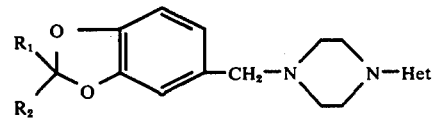

wherein:
   $R_1$ is selected from the group consisting of hydrogen and alkyl having 1 to 5 carbon atoms inclusive;
   $R_2$ is selected from the group consisting of alkyl having 1 to 5 carbon atoms inclusive and phenyl; or
   $R_1$ and $R_2$ together represent a polymethylenic chain —$(CH_2)_n$— wherein n is selected from 4, 5 and 6; and
   Het is selected from the group consisting of 2-thiazolyl, methyl-2-thiazolyl, phenyl-2-thiazolyl, and dimethyl-2-thiazolyl, and
   B. physiologically tolerable acid addition salts thereof.

2. A compound of claim 1 which is 5-[4-(2-thiazolyl)-1-piperazinyl] methyl-2-methyl benzo [d]-1,3-dioxole.

3. A compound of claim 1 which is 5-[4-(4-methyl-2-thiazolyl)-1-piperazinyl] methyl-2-methyl benzo [d]-1,3-dioxole.

4. A compound of claim 1 which is 5-[4-(4-phenyl-2-thiazolyl)-1-piperazinyl] methyl-2-methyl benzo [d]-1,3-dioxole.

5. A compound of claim 1 which is 5-[4-(4,5-dimethyl-2-thiazolyl)-1-piperazinyl]methyl-2-methyl benzo [d]-1,3-dioxole.

6. A compound of claim 1 which is 5-[4-(5-methyl-2-thiazolyl)-1-piperazinyl] methyl-2-methyl benzo [d]-1,3-dioxole.

7. A compound of claim 1 which is 5-[4-(5-phenyl-2-thiazolyl)-1-piperazinyl] methyl-2-methyl benzo [d]-1,3-dioxole.

8. A pharmaceutical composition containing as active principle a compound of claim 1 together with a suitable pharmaceutical carrier.

9. A method of treating a living animal body afflicted with vasoconstriction, or CNS depression, comprising the step of administering an amount of a compound of claim 1 effective for the alleviation of the said condition.

10. A method of treating a living animal body afflicted with parkinsonism comprising the step of administering an amount of a compound of claim 1 effective for the alleviation of said condition.

11. The method of claim 10, wherein dosages of 20 to 200 mg 1 to 5 times a day are administered.

12. The method of claim 11, wherein the compound is selected from the group consisting of:
   5-[4-(2-thiazolyl-1-piperazinyl] methyl-2-methyl benzo [d]-1,3-dioxole;
   5-[4-(4-methyl-2-thiazolyl)-1-piperazinyl] methyl-2-methyl benzo [d]-1,3-dioxole;
   5-[4-(4-phenyl-2-thiazolyl)-1-piperazinyl] methyl-2-methyl benzo [d]-1,3-dioxole;
   5-[4-(4,5-dimethyl-2-thiazolyl)-1-piperazinyl] methyl-2-methyl benzo [d]-1,3-dioxole;
   5-[4-(5-methyl-2-thiazolyl)-1-piperazinyl] methyl-2-methyl benzo [d]-1,3-dioxole;
   5-[4-(5-phenyl-2-thiazolyl)-1-piperazinyl] methyl-2-methyl benzo [d]-1,3-dioxole.

13. The method of claim 11, wherein the compound is 5-[4-(2-thiazolyl)-1-piperazinyl] methyl-2-methyl benzo [d]-1,3-dioxole.

* * * * *